US008338176B2

(12) United States Patent
Daadi et al.

(10) Patent No.: US 8,338,176 B2
(45) Date of Patent: Dec. 25, 2012

(54) DERIVATION OF NEURAL STEM CELLS FROM EMBRYONIC STEM CELLS

(75) Inventors: Marcel M. Daadi, Palo Alto, CA (US); Gary K. Steinberg, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1121 days.

(21) Appl. No.: 12/182,050

(22) Filed: Jul. 29, 2008

(65) Prior Publication Data
US 2009/0035284 A1 Feb. 5, 2009

Related U.S. Application Data

(60) Provisional application No. 60/952,834, filed on Jul. 30, 2007.

(51) Int. Cl.
*C12N 5/00* (2006.01)
(52) U.S. Cl. .......................... 435/377; 435/382; 435/387
(58) Field of Classification Search .................. None
See application file for complete search history.

(56) References Cited

U.S. PATENT DOCUMENTS

| | | | |
|---|---|---|---|
| 5,981,165 | A | 11/1999 | Weiss et al. |
| 6,284,539 | B1 | 9/2001 | Bowen et al. |
| 6,294,346 | B1 | 9/2001 | Weiss et al. |
| 6,887,706 | B2 | 5/2005 | Zhang et al. |
| 7,011,828 | B2 | 3/2006 | Reubinoff et al. |
| 7,015,037 | B1 | 3/2006 | Furcht et al. |
| 2005/0074880 | A1 | 4/2005 | Sang et al. |
| 2005/0214941 | A1 | 9/2005 | Bhonsale et al. |
| 2005/0221479 | A1 | 10/2005 | Nakayama et al. |
| 2005/0255589 | A1 | 11/2005 | Reubinoff et al. |
| 2005/0260747 | A1 | 11/2005 | Reubinoff et al. |
| 2006/0030041 | A1 | 2/2006 | Furcht et al. |
| 2006/0078543 | A1 | 4/2006 | Reubinoff et al. |
| 2006/0194315 | A1 | 8/2006 | Condie et al. |
| 2006/0252149 | A1 | 11/2006 | Zeigler |
| 2007/0059823 | A1 | 3/2007 | Verfaillie et al. |
| 2007/0155012 | A1 | 7/2007 | Privat et al. |

FOREIGN PATENT DOCUMENTS

WO 2004/103394 A2 12/2004

OTHER PUBLICATIONS

PCT International Search Report and Written Opinion dated Dec. 4, 2008, for International Application No. PCT/US2008/077407.
Engele J, Shubert D, Bohn MC, Conditioned media Derived From Glial Cell Lines Promote Survival and Differentiation of Dopaminergic Neurons in Vitro: Role of Mesencephalic Glia, Journal of Neuroscience Research 30:359-371 (1991).
Arenas E, Stem Cells in the Treatment of Parkinson's Disease, Brain Research Bulletin 57:795-808 (2002).
Buytaert-Hoefen KA, Alvarez E, Freed CR, Generation of Tyrosine Hydroxylase Positive Neurons From Human Embryonic Stem Cells After Co-Culture With Cellular Substrates and Exposure to GDNF, Stem Cells 22:669-674 (2004).
Carpenter MK, Cui X, Hu ZY, Jackson J, Sherman S, Seiger A, Wahlberg LU, In Vitro Expansion of a Multipotent Population of Human Neural Progenitor Cells, Experimental Neurology 158:265-278 (1999).
Carvey PM, Ling ZD, Sortwell CE, Pitzer MR, McGUIRE SO, Storch A, Collier TJ, A Clonal Line of Mesencephalic Progenitor Cells Converted to Dopamine Neurons by Hematopoietic Cytokines: A Source of Cells for Transplantation in Parkinson's Disease, Experimental Neurology 171:98-108 (2001).
Daadi M, Arcellana-Panlilio MY, Weiss S, Activin Co-Operates With Fibroblast Growth Factor 2 to Regulate Tyrosine Hydroxylase Expression in the Basal Forebrain Ventricular Zone Progenitors, Neuroscience 86:867-880 (1998).
Daadi M, Weiss S, Generation of Tyrosine Hydroxylase-Producing Neurons From Precursors of the Embryonic and Adult Forebrain, The Journal of Neuroscience, 19:4484-4497 (1999).
Dunnett SB, Bjorklund A, Lindvall O, Cell Therapy in Parkinson's Disease—Stop or Go?, Nature Reviews Neuroscience 2:365-369 (2001).
Freed CR, Greene PE, Breeze RE, Tsai WY, DuMouchel W, Kao R, Dillon S, Winfield H, Culver S, Trojanowski JQ, Eidelberg D, Fahn S, Transplantation of Embryonic Dopamine Neurons For Severe Parkinson's Disease, The New England Journal of Medicine 344:710-719 (2001).
Kawasaki H, Mizuseki K, Nishikawa S, Kaneko S, Kunwana Y, Nakanishi S, Nishikawa SI, Sasai Y, Induction of Midbrain Dopaminergic Neurons From ES Cells by Stromal Cell-Derived Inducing Activity, Neuron 28:31-40 (2000).
Kim JH, Auerback JM, Rodriquez-Gomez JA, Velasco I, Gavin D, Lumelsky N, Lee Sh, Nguyen J, Sanchez-Pernaute R, Bankiewicz K, McKay R, Dopamine Neurons Derived From Embryonic Stem Cells Function in an Animal Model of Parkinson's Disease, Nature 418:50-56 (2002).

(Continued)

*Primary Examiner* — Deborah Crouch
(74) *Attorney, Agent, or Firm* — Bozicevic, Field & Francis LLP; Pamela J. Sherwood (57) ABSTRACT

Provided is a method for the derivation of neural stem cells (NSCs) from embryonic stem cells (ESCs) and the use of the NSCs for treatment of various neural disorders. The NSCs that are derived from the ESCs are tissue-specific multipotent NSCs with a stable growth rate, unlimited self-renewal capacity, and a predictable differentiation profile. Being both non-tumorigenic and engraftable, the NSCs of the present invention have utility in repopulation stroke-damaged tissue. The NSCs of the present invention may be differentiated to produce tyrosine-hydroxylase expressing neurons, which may be used as a source of dopaminergic neurons for subjects suffering from a condition characterized by dopaminergic dysfunction, such as Parkinson's disease.

17 Claims, 10 Drawing Sheets
(7 of 10 Drawing Sheet(s) Filed in Color)

OTHER PUBLICATIONS

Lee CS, Cenci MA, Schulzer M, Bjorklund A, Embryonic Ventral Mesencephalic Grafts Improve Levodopa-Induced Dyskinesia in a Rat Model of Parkinson's Disease, Brain 123 (Pt 7):1365-1379 (2000).

Lindvall O, Stem Cells for Cell Therapy in Parkinson's Disease, Pharmacological Research 47:279-287 (2003).

Ling ZD, Potter ED, Lipton JW, Carvey PM, Differentiation of Mesencephalic Progenitor Cells Into Dopaminergic Neurons by Cytokines, Experimental Neurology 149:411-423 (1998).

Perrier AL, Tabar V, Barberi T, Rubio ME, Bruses J, Topf N, Harrison NL, Studer L, Derivation of Midbrain Dopamine Neurons From Human Embryonic Stem Cells, Proceedings of the National Academy of Sciences of the United States of America 101:12543-12548 (2004).

Potter ED, Ling ZD, Carvey PM, Cytokine-Induced Conversion of Mesencephalic-Derived Progenitor Cells Into Dopamine Neurons, Cell Tissue Res 296:235-246 (1999).

Roy NS, Cleren C, Singh SK, Yang L, Beal MF, Goldman SA, Functional Engraftment of Human ES Cell-Derived Dopaminergic Neurons Enriched by Coculture With Telomerase-Immortalized Midbrain Astrocytes, Nature Medicine vol. 12, No. 11, pp. 1259-1268 (2006).

Sakurada K, Ohshima-Sakurada M, Palmer TD, Gage FH, Nurr1, An Orphan Nuclear Receptor, Is a Transcriptional Activator of Endogenous Tyrosine Hydroxylase in Neural Progenitor Cells Derived From the Adult Brain, Development 126:4017-4026 (1999).

Saucedo-Cardenas O, Quintana-Hau JD, Le WD, Smidt MP, Cox JJ, De Mayo F, Burbach JP, Conneely OM, Nurr1 Is Essential for the Induction of the Dopaminergic Phenotype and the Survival of Ventral Mesencephalic Late Dopaminergic Precursor Neurons, Proceedings of the National Academy of Sciences of the United States of America 95:4013-4018 (1998).

Storch A, Paul G, Csete M, Boehm BO, Carvey PM, Kupscha, Schwarz J, Long-Term Proliferation and Dopaminergic Differentiation of Human Mesencephalic Neural Precursor Cells. Experimental Neurology 170:317-325 (2001).

Studer L, Csete M, Lee SH, Kabbani N, Walikonis J, Wold B, McKay R, Enhanced Proliferation, Survival, and Dopaminergic Differentiation of CNS Precursors in Lowered Oxygen, The Journal of Neuroscience 20:7377-7383 (2000).

Svendsen CN, Caldwell MA, Shen J, ter Borg MG, Rosser AE, Tyers P, Karmiol S, Dunnett SB, Long-Term Survival of Human Central Nervous System Progenitor Cells Transplanted Into a Rat Model of Parkinson's Disease, Experimental Neurology 148:135-146 (1997).

Wagner J, Akerud P, Castro DS, Holm PC, Canals JM, Snyder EY, Perlmann T, Arenas E, Induction of a Midbrain Dopaminergic Phenotype in Nurr1-Overexpressing Neural Stem Cells by Type 1 Astrocytes, Nature Biotechnology 17:653-659 (1999).

Yan J, Studer L, McKay RD, Ascorbic Acid Increases the Yield of Dopaminergic Neurons Derived From Basic Fibroblast Growth Factor Expanded Mesencephalic Precursors, Journal of Neurochemistry 76:307-311 (2001).

Ye W, Shimamura K, Rubenstein JL, Hynes MA, Rosenthal A, FGF and SHH Signals Control Dopaminergic and Serotonergic Cell Fate in the Anterior Neural Plate, Cell 93:755-766 (1998).

Zetterstrom RH, Solomin L, Jansson L, Hoffer BJ, Olson L, Perlmann T, Dopamine Neuron Agenesis in Nurr1-Deficient Mice, Science 276:248-250 (1997).

Hoffman LM, Carpenter MK, Characterization and Culture of Human Embryonic Stem Cells, Nature Biotechnology 23:699-708 (2005).

Carpenter MK, Inokuma MS, Denham J, Mujitaba T, Chiu CP, Rao MS, Enrichment of Neurons and Neural Precursors From Human Embryonic Stem Cells, Experimental Neurology 172:383-397 (2001).

Reubinoff BE, Itsykson P, Turetsky T, Pera MF, Reinhartz E, Itzik A, Ben-Hur T, et al, Neural Progenitors From Human Embryonic Stem Cells, Nature Biotechnology 19:1134-1140 (2001).

Zhang SC, Wernig M, Duncan ID, Brustle O, Thomson JA, In Vitro Differentiation of Transplantable Neural Precursors From Human Embryonic Stem Cells, Nature Biotechnology 19:1129-1133 (2001).

Brederlau A, Correia AS, Anisimov SV, Elmi M, Paul G, Roybon L, Morizane A, Bergquist F, Riebe I, Nannmark U, Carta M, Hanse E, Takahashi J, Sasai Y, Funa K, Brundin P, Eriksson P, Li JY, Transplantation of Human Embryonic Stem Cell-Derived Cells to a Rat Model of Parkinson's Disease: Effect of in Vitro Differentiation on Graft Survival and Teratoma Formation, Stem Cells 24:1433-1440 (2006).

Yan Y, Yang D, Zarnowska Ed, Du Z, Werbel B, Valliere C, Pearce RA, Thomson JA, Zhang SC, Directed Differentiation of Dopaminergic Neuronal Subtypes From Human Embryonic Stem Cells, Stem Cells 23:781-790 (2005).

Uchida N, Buck DW, He D, Reitsma MJ, Masek M, Phan TV, Tsukamoto AS, Gage FH, Weissman RL, Direct Isolation of Human Central Nervous System Stem Cells, Proceedings of the National Academy of Sciences of the United States of America 97:14720-14725 (2000).

Reynolds BA, Weiss S, Generation of Neurons and Astrocytes From Isolated Cells of the Adult Mammalian Central Nervous System, Science 255:1707-1710 (1992).

He Z; LI JJ; Zhen CH, Feng LY; Ding XY, Effect of Leukemia Inhibitory Factor on Embryonic Stem Cell Differentiation: Implications for Supporting Neuronal Differentiation; Acta Pharmacologica Sinica 27(1):80-90 (2006).

Schwartz PH, Bryant PJ, Fujatj, Su H, O'Dowd DK, Klassen H, Isolation and Characterization of Neural Progenitor Cells From Post-Mortem Human Cortex, Journal of Neuroscience Research 74(6):838-851 (2003).

DERIVATION OF NEURAL STEM CELLS FROM EMBRYONIC STEM CELLS

CROSS-REFERENCE TO RELATED APPLICATIONS

This application claims priority under 35 U.S.C. §119(e) to U.S. Provisional Patent Application No. 60/952,834, filed on Jul. 30, 2007, which is incorporated herein by reference in its entirety.

STATEMENT OF GOVERNMENT SUPPORT

This invention was made with Government support under Contract Nos. NIH/2 ROI NS27292-08A2 and NIH/3 P01 NS37520 awarded by the National Institute of Health. The Government has certain rights in the invention.

TECHNICAL FIELD

The present invention relates generally to techniques for manipulating embryonic stem cells. More specifically, the invention relates to a method for derivation of neural stem cells (NSCs) from embryonic stem cells (ESCs) and the use of the ESC-derived NSCs to treat various neural conditions, disorders, and diseases.

BACKGROUND OF THE INVENTION

Stem cells are primal cells that are found in all multicellular organisms. Stem cells have the ability to self-renew through mitotic cell division and can differentiate into a diverse range of specialized cell types. The three broad categories of mammalian stem cells are embryonic stem cells, adult stem cells, and cord blood stem cells. ES cells are derived from the inner cell mass of pre-implantation embryos, i.e., blastocysts. Human embryos reach the blastocyst stage 4-5 days post fertilization, at which time they consist of 50-150 cells. Adult stem cells are found in adult tissue. Cord blood stem cells are derived from the umbilical cord, which is rich in hematopoietic stem cells, i.e., stem cells that will form all cellular components of blood.

ES cells are pluripotent, meaning that they are able to differentiate into all of the somatic cell types of the three primary germ layers: the ectoderm, the endoderm, and the mesoderm. ES cells are the ultimate source for each of the more than 220 cell types in the adult body. When given no stimuli for differentiation, i.e. when grown in vitro, ES cells have the potential for indefinite expansion with continued plutipotency throughout each cell division.

Like embryonic stem cells, adult stem cells have the potential to self-renew indefinitely; however, unlike embryonic stem cells, adult stem cells are not pluripotent, rather, they are multipotent, meaning that they are able to differentiate into some, but not all specialized cells. Closely related to adult stem cells are adult progenitor cells. Like adult stem cells, adult progenitor cells are multipotent; however, unlike adult stem cells, adult progenitor cells cannot renew indefinitely. Having limited self-renewal abilities, adult progenitors differentiate into mature cells after several rounds of cell division. Examples of adult progenitors are satellite cells found in muscle and neural stem progenitor cells. Both adult stem cells and adult progenitors are found throughout the adult body and act as repair system for the organism by repopulating a limited number of cells types in the organism.

As stem cells can be readily grown and transformed in vitro into specialized cells with characteristics consistent with cells of various tissues, their use in medical therapies is of great interest. In order to effectively treat neural conditions with embryonic stem cells, there is a need in the art for an effective and efficient method to produce a homogeneous population of neural stem cells from embryonic stem cells. The following patent documents describe the isolation of neural stem cells from ES and adult progenitor cells.

U.S. Pat. No. 7,011,828 and U.S. Patent Publication Nos. 2005/0260747 A1 and 2006/0078543 A1 all to Reubinoff et al. teach the proliferation of an enriched population of embryonic stem cells, which are induced to differentiate in vitro to neural progenitor cells, neurons, and/or glial cells (collectively referred to as "neural cells").

U.S. Pat. No. 7,015,037 and U.S. Patent Publication No. 2006/0030041 A1 both to Furcht et al. teach the differentiation of multipotent adult stem cells (MASCs) to form glial, neuronal, or oligodendrocyte cell types using growth factors, chemokines, and cytokines such as EGF, PDGF-BB, FGF2, and FGF-9.

U.S. Patent Publication No. 2006/0252149 to Zeigler teaches the maintenance of central nervous system (CNS) cells outside of an organism that retain the ability to proliferate and remain in a state of being able to differentiate as a result of exposure in culture to soluble laminin alone or together with one or more laminin associated factors (LAFs) and one or more of the CNS mitogens EGF, bFGF (also referred to as FGF2), and LIF.

U.S. Pat. No. 6,887,706 to Zhang et al. teaches a method of differentiating embryonic stem cells into neural precursor cells using the growth factor FGF2. In vitro differentiation of the ES cell-derived neural precursors was induced by withdrawal of FGF2 and plating on ornithine and laminin substrate.

U.S. Patent Publication No. 2007/0059823 A1 to Verfaillie et al. teaches a method for inducing ES cells and MASCs to differentiate into neuronal cells by culturing the stem cells initially with bFGF and later with FGF8, Sonic Hedgehog, brain-derived neutrotrophic factor, and astrocytes. Verfaillie et al. disclose that where it is desired for the stem cells to remain in an undifferentiated state, the media can contain supplements such as EGF, platelet derived growth factor (PDGF), and LIF.

U.S. Patent Publication No. 2005/0214941 A1 to Bhonsale et al. teaches a method for improving the growth rate of human fetal brain stem cells by culturing human neural stem cells ("hNSCs") with bFGF, EGF, and LIF. Bhonsale et al. also provide a method for increasing the rate of proliferation of neural stem cell cultures and increasing the number of neurons in the differentiated cell population by culturing the hNSCs on a surface coated with polyornithine and fibronectin.

None of the foregoing patents and/or patent publications teaches the proliferation of a homogeneous population of neural stem cells with unlimited self-renewal capability derived from embryonic stem cells; accordingly, there remains a need in the art for an effective and efficient method of producing an unlimited supply of a homogeneous population of neural cells from embryonic stem cells.

SUMMARY OF THE INVENTION

The present invention overcomes the aforementioned need in the art by providing a method of deriving neural stem cells (NSCs) from embryonic stem cells (ESCs). The present invention also provides methods of use of the NSCs of the present invention for the treatment of various neural conditions, disorders, and diseases.

In one aspect of the invention, there is providing a method for deriving a homogeneous population of NSCs comprising culturing ESCs as spheres in media containing epidermal growth factor (EGF), basic fibroblast growth factor (bFGF), and leukemia inhibitory factor (LIF).

In another aspect of the invention, there is provided a method of deriving a homogeneous population of NSCs from ESCs comprising the steps of: (a) culturing an ESC line in media comprising EGF, bFGF, and LIF until spheres (primary spheres) form in the media; (b) selecting and plating the primary spheres in a cell culture container in media comprising EGF, bFGF, and LIF until the spheres attach to the container and the ESCs form clusters; (c) removing the clusters from the culture container and replating the clusters as secondary spheres in a container with media comprising EGF, bFGF, and LIF until the spheres attach to the container.

In a further aspect of the invention, there is provided a method of repopulating stroke damaged tissue with neural cells comprising grafting NSCs obtained according to the method of the present invention into lesioned brain of a subject that has suffered a stroke.

In yet another aspect of the invention, there is provided a method of inducing NSCs to express genes of mid-brain dopaminergic lineage comprising culturing the NSCs in glial conditioned media comprising mitogenic factors EGF, bFGF, and LIF.

In still a further embodiment of the invention, there is provided a method of deriving TH-expressing neurons from NSCs comprising the steps of: (a) inducing the mid-brain dopaminergic gene expressing NSCs of the present invention to differentiate to neurons; and (b) culturing the neurons in glial conditioned media comprising at least one fibroblastic growth factor (FGF) family member.

In another aspect of the invention, there is provided a method of providing dopaminergic neurons to a subject suffering from dopaminergic dysfunction comprising administering the tyrosine hydroxylase expressing (TH-expressing) neurons of the present invention to the subject's nervous system.

In a further aspect of the invention, there is provided a method of screening a drug for therapeutic effects on dopaminergic cells comprising treating the TH-expressing neurons of the present invention with the drug and measuring the TH-expressing neurons for responses selected from the group consisting of dopaminergic response, cell survival, phenotypic changes, and genotypic changes.

Additional aspects, advantages and features of the invention will be set forth, in part, in the description that follows, and, in part, will become apparent to those skilled in the art upon examination of the following, or may be learned by practice of the invention.

BRIEF DESCRIPTION OF THE DRAWINGS

This patent document contains more than one drawing executed in color. Copies of this patent or patent application publication with color drawings will be provided by the Office upon request and payment of the necessary fee.

FIGS. 1a-1f are photographs of the isolation and purification of NSCs from hESCs according to the method of the present invention; FIG. 1a shows hESCs.

FIG. 2a-2c shows photographs that demonstrate the homogeneity of the NSCs cultured according to the method of the present invention.

FIGS. 4a-4c are photographs showing the clonal self-renewal ability of the isolated NSCs of the present invention over a 7-day culture period, which are identified with the following markers: nuclear marker DAP1 (first column); neural stem cell marker Nestin (second column); stem cell marker SSEA4 (third column); and all three markers together (last column).

FIGS. 5a and 5b are graphs showing the long-term growth of the NSCs of the present invention.

FIG. 15a and 15b show photographs of tyrosine hydroxylase (TH) expressing NSCs plated on poly-L-ornithine coated glass coverslips.

DETAILED DESCRIPTION OF THE INVENTION

Set forth below is a description of what are currently believed to be the preferred embodiments and best examples of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The following detailed description includes some definitions that are helpful for understanding the invention and the appended claims. It is to be understood that the definitions are provided solely for purposes of clarity and are not intended to limit the scope of the invention as described or as claimed.

The terms "cell culture container," "culture container," and/or "container" are used to refer to a receptacle comprised of a suitable material upon which the ESCs and NSCs of the present invention may adhere and grow. Examples of suitable materials for cell culture containers include without limitation: glass, controlled pore glass, functionalized glass, ceramics, silica, silica-based materials, polystyrene, polystyrene latex, polyvinyl chloride, polyvinylidene fluoride, polyvinyl acetate, polyvinyl pyrrolidone, polyacrylonitrile, polyacrylamide, polymethyl methacrylate, polytetrafluoroethylene, polyethylene, polypropylene, and polycarbonate, divinylbenzene styrene-based polymers, celluloses (such as nitrocellulose), cellulosic polymers, polysaccharides, and metals.

The term "substrate" refers to a biological substrate, which is any solid or semi-solid surface upon which a biological organism grows. Examples of suitable substrates for use with the present invention include without limitation, glass coverslips (see, Examples 3 and 6) and microtiter wells or sheets produced with any of the following materials: controlled pore glass, functionalized glass, ceramics, silica, silica-based materials, polystyrene, polystyrene latex, polyvinyl chloride, polyvinylidene fluoride, polyvinyl acetate, polyvinyl pyrrolidone, polyacrylonitrile, polyacrylamide, polymethyl methacrylate, polytetrafluoroethylene, polyethylene, polypropylene, and polycarbonate, divinylbenzene styrene-based polymers, celluloses (such as nitrocellulose), cellulosic polymers, polysaccharides, and metals.

The term "glial conditioned media" refers to a cell culture media that has been conditioned with glial cells and/or factors, proteins, or peptides associated with glial cells. "Glial cells" are known by those of skill in the art to include astrocytes, oligodendrocytes, ependymal cells, glioma cells, and radial glial cells; accordingly, it is to be understood that within the context of the present invention, the "glial conditioned media" of the present invention may be prepared using any type of glial cell, and/or factors, proteins or peptides obtained from any type of glial cell.

As used herein, the term "subject" is meant to include any species that may benefit from the therapy at issue. Subjects contemplated under the invention include all mammalian species including humans.

The present invention relates to methods for the derivation of neural stem cells (NSCs) from embryonic stem cells (ESCs) and the use of the NSCs for treatment of various neural disorders. The ESCs that are used to derive the NSCs may be obtained from any mammalian species including humans (hESCs). The NSCs that are derived from the ESCs are tissue-specific multipotent NSCs with a stable growth rate, unlimited self-renewal capacity, and a predictable differentiation profile. Being both non-tumorigenic and engraftable, the NSCs of the present invention have the capacity for a wide range of therapeutic uses.

In one aspect of the invention, a homogeneous population of NSCs is derived by culturing ESCs as spheres in media containing epidermal growth factor (EGF), basic fibroblast growth factor (bFGF), and leukemia inhibitory factor (LIF).

In another aspect of the invention, the homogeneous population of NSCs is derived from ESCs comprising the steps of: (a) culturing an ESC line in media comprising EGF, bFGF, and LIF until spheres (primary spheres) form in the media; (b) selecting and plating the primary spheres in a cell culture container in media comprising EGF, bFGF, and LIF until the spheres attach to the container and the ESCs form clusters; (c) removing the clusters from the culture container and replating the clusters as secondary spheres in a container with media comprising EGF, bFGF, and LIF.

In one embodiment of the invention, the secondary spheres are allowed to attach to the container and step (c) is repeated with subsequent spheres until a population of cells of a desired size is obtained. The spheres may be passaged indefinitely by techniques known in the art, such as with collagenase, which is typically used to dissociate cells from tissues, or trypsin-EDTA, which is typically used to dissociate adherent cells. As described in Example 1, at some point in the passaging of the spheres, the adherent properties of the cells change and the cells begin to grow as a monolayer with each individual cell having the ability to renew indefinitely. As described in Example 2 single-cells dissociated from the spheres tested positive for the neural cell progenitor marker nestin indicating that they are self-renewing NSCs.

The EGF, bFGF, and LIF may be added to the media in concentrations that may range from 1 ng/mL to 1 µg/mL for each of the mitogenic growth factors. The concentrations used in the Examples are 20 ng/mL EGF, 10 ng/mL bFGF, and 10 ng/mL LIF; however, these concentrations are not meant to be limiting and other concentrations of the mitogenic factors that are capable of achieving a homogeneous population of NSCs according to the method set forth herein may be used. The media that may be used to culture the ESCs is preferably serum free media.

The population of cells obtained by the method of the present invention may be tested for NSCs with a neural progenitor stem cell marker. Examples of neural progenitor stem cell markers are available through Chemicon (now a part of Millipore, Temecula, Calif.) or Invitrogen (Carlsbad, Calif.). Such markers include, without limitation, nestin (neuroepithelial stem cell marker); MSi-1; N-cadherin; Sox1; Sox2; and Tau (neurofibrillary tangle protein).

In still a further embodiment, the NSCs are induced to differentiate by removal of EGF, bFGF, and LIF from the culture media and plating on a substrate. The substrate may be coated with an ionically charged substance selected from the group consisting of poly-L-ornithine (PLO), poly-D-lysine, fibronectin, laminin, and MATRIGEL®.

In a further embodiment, the induced cells differentiate to give rise to neurons, astrocytes, and oligodendrocytes. The differentiated cells may be identified through expression of any markers known in the art to identify the cells in question.

Examples of markers that may be used to identify neurons, astrocytes, and oligodendrocytes are listed on-line through the National Institute of Health at the following website: "http://stemcells.nih.gov/info/scireport/appendixe.asp#eii," and are commercially available through Chemicon (now a part of Millipore, Temecula, Calif.) or Invitrogen (Carlsbad, Calif.). The following list of markers is intended to be illustrative and not limiting of the markers that may be used to identify neurons, astrocytes, and oligodendrocytes.

Neurons may be identified by expression of neuronal markers Tuj1 (β-III-tubulin); MAP-2 (microtubule associated protein 2, other MAP genes such as MAP-1 or -5 may also be used); anti-axonal growth clones; ChAT (choline acetyltransferase); CgA (anti-chromagranin A); DARRP (dopamine and cAMP-regulated phosphoprotein); DAT (dopamine transporter); GAD (glutamic acid decarboxylase); GAP (growth associated protein); anti-HuC protein; anti-HuD protein; α-internexin; NeuN (neuron-specific nuclear protein); NF (neurofilament); NGF (nerve growth factor); γ-NSE (neuron specific enolase); peripherin; PH8; PGP (protein gene product); SERT (serotonin transporter); synapsin; Tau (neurofibrillary tangle protein);anti-Thy-1; TRK (tyrosine kinase receptor); TRH (tryptophan hydroxylase); anti-TUC protein; TH (tyrosine hydroxylase); VRL (vanilloid receptor like protein); VGAT (vesicular GABA transporter); VGLUT (vesicular glutamate transporter).

Astrocytes may be identified by expression of astrocyte markers GFAP (glial fibrillary acid protein); ASTO-1 (anti-astrocyte marker); or S-100 (anti-S-100 protein).

Oligodendrocytes may be identified by expression of oligodendrocyte markers GC (galactocerebrocide, also referred to as GalC); MBP (myelin basic protein); CNPase (2',3'-cyclic nucleotide 3'-phosphodiesterase [or -phosphohydrolase]); or the oligodendrocyte markers NSP, RIP, MOSP, O1 or O4.

Figure 6:
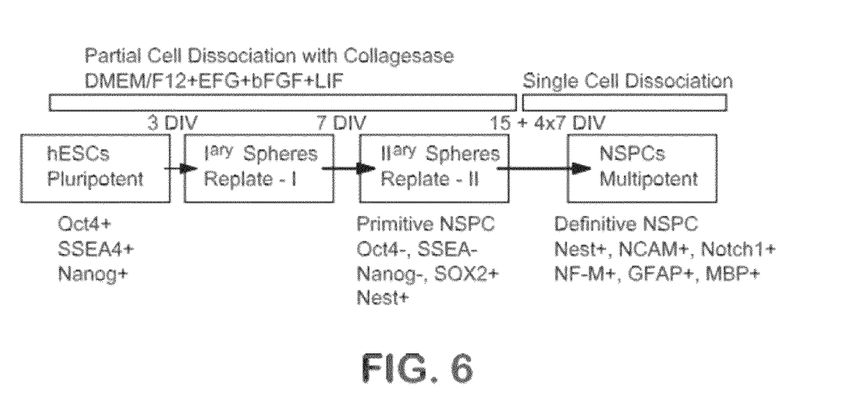
FIG. 6 is a flow chart of the method of the present invention.
Figure 7:
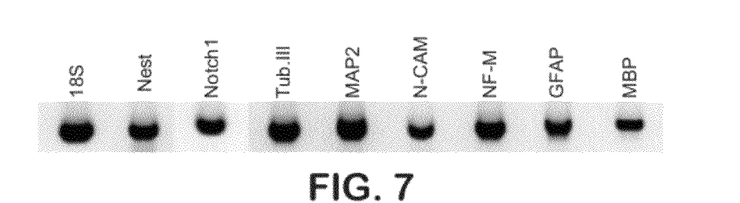
FIG. 7 is a gel showing NSC expression of the neural specific transcripts nestin and Notch 1 and transcript expression for neurons (β-tubulin class III [Tub.III], MAP-2, N-CAM, and medium-sized neurofilament NF-M), astrocytes (GFAP), and oligodendrocytes (MBP).
Figure 8:
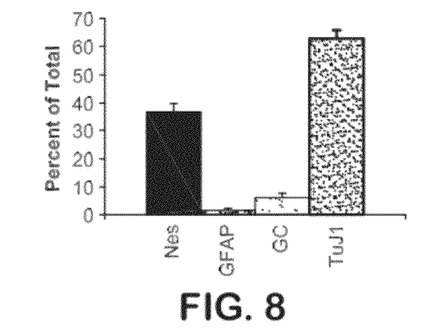
FIG. 8 is a bar graph showing quantitative analysis of immunostained cultures for the three neural cell types with nestin (Nes) testing for neural cells generally, GFAP for astrocytes, GC for oligodendrocytes, and Tuj1 for neurons.
Figure 9:
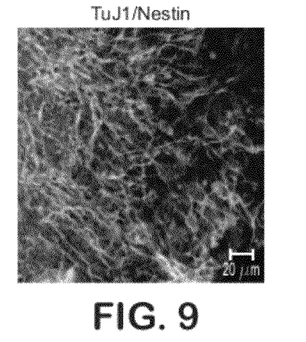
FIG. 9 is a photograph showing NSC cultures double-immunostained for Tuj1 (bright stain) and nestin (dark stain).
Figure 10:
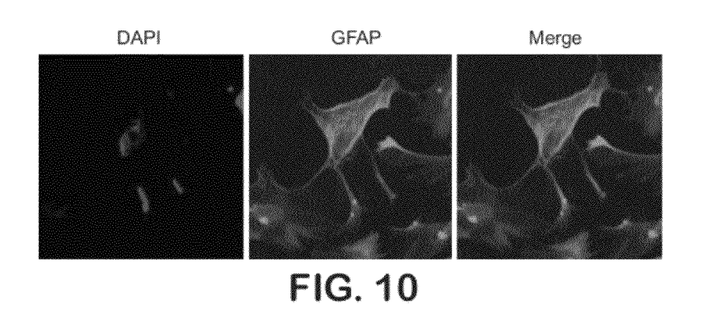
FIG. 10 shows photographs of NSC-derived GFAP expressing astrocytes.
Figure 11:
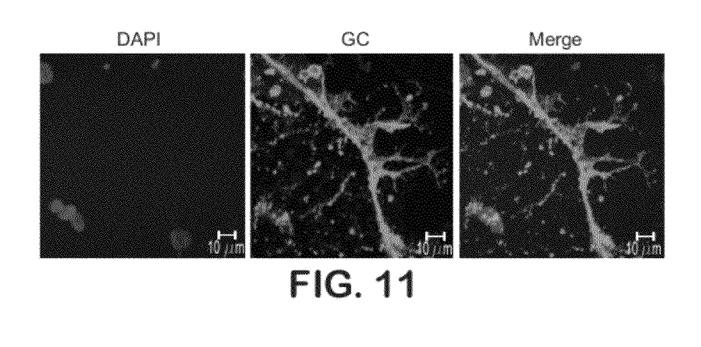
FIG. 11 shows photographs of NSC-derived GC-expressing oligodendrocytes.
Figure 12A:
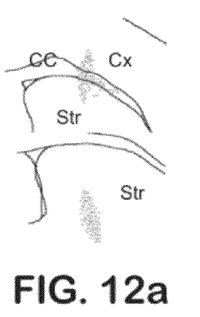
FIG. 12a is a diagram illustrating the distribution of grafted NSCs immunostained with the human specific anti-human nuclei antibody hNuc (CC=corpus collosum; Cx=cerebral cortex; and Str=striatial parenchyma).
Figure 12B:
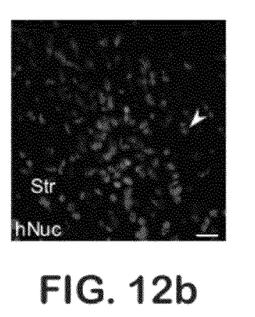
FIG. 12b is a photograph showing hNuc NSCs dispersed in the striatial parenchyma (Str).
Figure 12C:
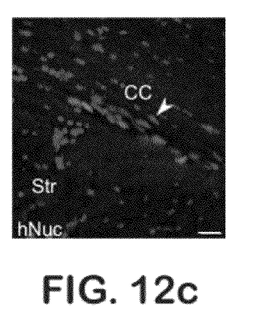
FIG. 12c is a photograph showing hNuc NSCs dispersed in the corpus collosum (CC).
Figure 13A:
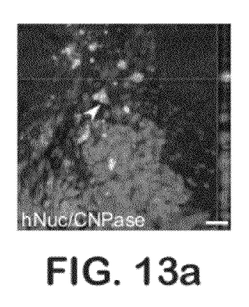
FIG. 13a shows photographs of brain sections processed for double immunocytochemistry with anti-hNuc and the oligodendrocyte specific marker CNPase.
Figure 13B:
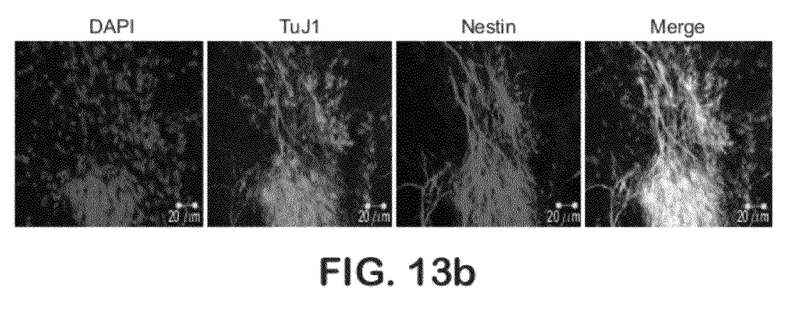
FIG. 13b shows photographs of brain sections processed for double immunocytochemistry with human specific nestin antibody and Tuj1 for neurons.
Figure 14A:
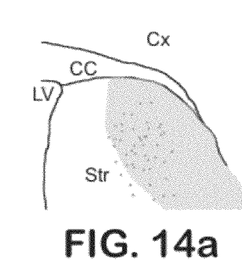
FIG. 14a is an illustration of the transplantation of NSCs into stroked rats; the dotted area represents the extent of focal ischemia in the rats.
Figure 14B:
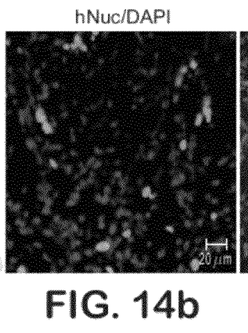
FIG. 14b is a photograph of the frontal section of the brain of a stroked rat, which was immunoprocessed for hNuc (human nuclear marker; bright stain).
Figure 14C:
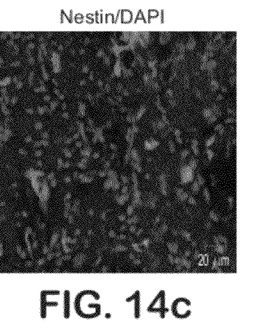
FIG. 14c is a photograph of the frontal section of the brain of a stroked rat, which was immunoprocessed for Nestin (light stain).
Figure 14D:
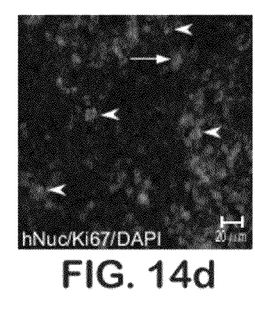
FIG. 14d is a photograph of the frontal section of the brain of a stroked rat, which was double immunoprocessed for hNuc (left pointing arrows) and Ki67 (cell proliferation marker; right pointing arrow).
Figure 14E:
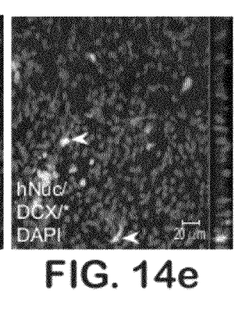
FIG. 14e is a photograph of the frontal section of the brain of a stroked rat, which was double immunoprocessed for hNuc (bright stains in upper right quadrant and lower left quadrant) and DCX (double cortin; left pointing arrows).
Figure 14F:
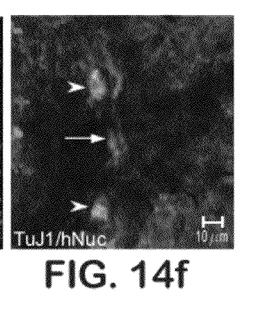
FIG. 14f is a photograph of the frontal section of the brain of a stroked rat, which was double immunoprocessed for Tuj1 (stemless arrows) and hNuc (stemmed arrow).
Figure 15A:
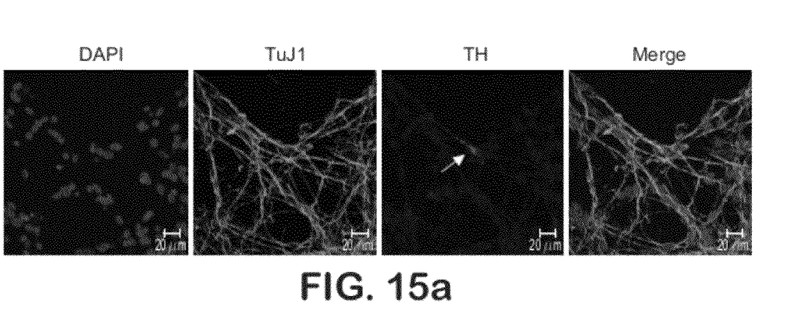
FIG. 15a is a control culture and FIG. 15b is a culture treated with B49 glial cell conditioned media (CM) and growth factors (GFs) bFGF (20 ng/mL), EGF (10 ng/mL), and LIF (10 ng/mL) for 10 days. Fixed cultures were double immunoprocessed for TH and the neuronal marker Tuj1. The CM+GF cultures (FIG. 15b) showed significantly higher numbers of TH-immunoreactive cells (see, arrows in third panels).
Figure 15B:
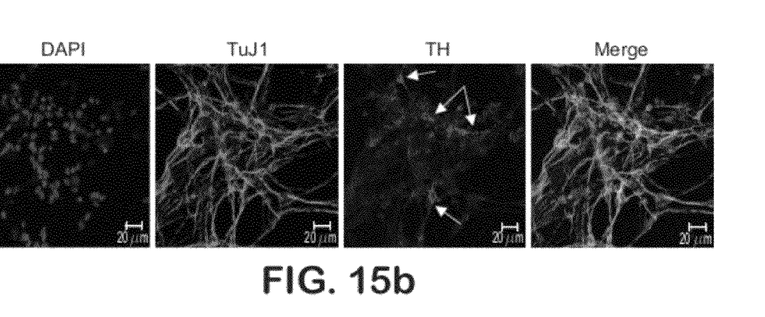
Figure 16A:
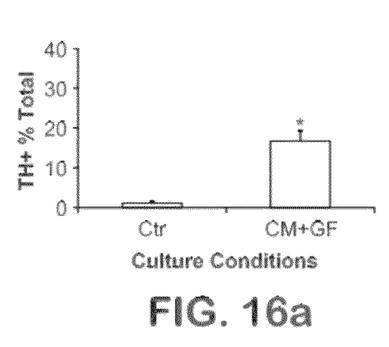
FIG. 16a is a bar graph that plots culture conditions, i.e., control and CM against the percent TH-immunoreactive cells in live NSCs.
Figure 16B:
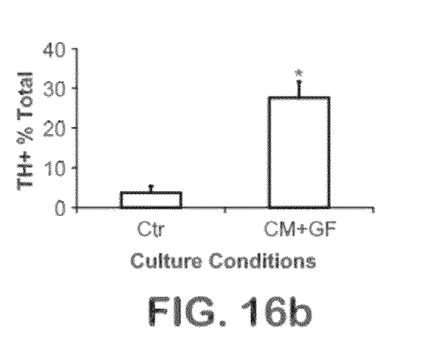
FIG. 16b is a bar graph that plots culture conditions, i.e., control and CM against the percent of TH-immunoreactive cells in Tuj1 stained neurons.
Figure 17:
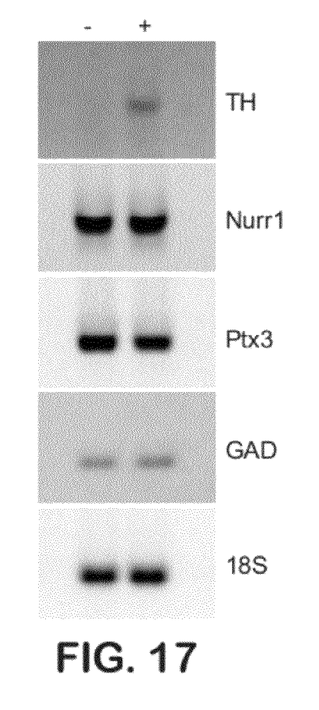
FIG. 17 is a photograph of a gel showing RNA samples extracted from NSCs cultured in the absence (−) or presence (+) of CM, bFGF, EGF, and LIF for 10 days. The amount of TH, Nurr1, Ptx3, GAD, and 18S in the RNA was determined by RT-PCR. The CM+GF treated cultures (+) showed a selective increase in TH transcript.

Under the proper culture conditions, the NSCs of the present invention can be induced to express specific neural stem genes, such as for example, genes of the mid-brain dopaminergic lineage, e.g., Nurr1 and Ptx3. The NSCs of the present invention may be induced to express mid-brain dopaminergic genes by culturing the NSCs in glial conditioned media comprising mitogenic factors EGF, bFGF, and LIF. As shown in Example 5, NSCs exposed to bFGF+glial cell conditioned media expressed significant amounts of Nurr1 and Ptx3 (FIG. 6).

The NSCs of the present invention may be induced to differentiate into TH-expressing neurons. TH is a known marker for dopamine (DA) neurons. In one embodiment of the invention, the TH-expressing neurons of the present invention are derived by: (a) inducing mid-brain dopaminergic gene expression in the NSCs of the present invention to differentiate to neurons; and (b) culturing the neurons in media conditioned to induce the neurons to express TH. In order to induce TH expression, the neurons are cultured with at least one mitogenic factor in glial conditioned media. The at least one mitogenic growth factor may be comprised of a member of the fibroblastic growth factor (FGF) family, i.e., FGF1, FGF2 (also known as bFGF or basic FGF), FGF3, FGF4, FGF5, FGF6, FGF8, FGF9, and FGF 10 to FGF20. In one embodiment, the at least one mitogenic growth factor is comprised of bFGF. In another embodiment, the bFGF further comprises one or both of EGF and LIF. While not intending to be bound by theory, it is believed that the glial soluble factors in the glial conditioned media act synergistically with the at least one mitogenic factor, such as for example, bFGF, to instruct forebrain derived stem cell progeny (i.e., NSCs) to express TH.

Figure 5A:
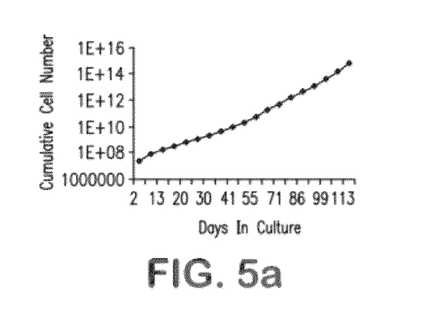
FIG. 5a plots days in culture against cumulative cell number and FIG. 5b plots days in culture against cumulative population doubling.
Figure 5B:
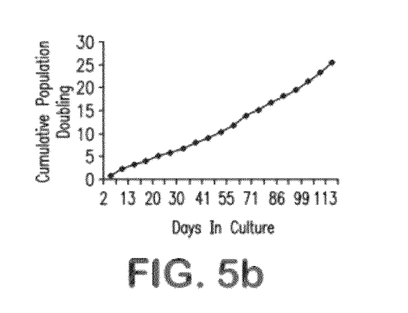

The NSCs may be induced to differentiate by culturing the NSCs in media lacking the mitogenic factors that keep the NSCs in an undifferentiated state (e.g., for a period of approximately 2 hours). As shown in Example 6, exposure of adherent NSCs of the present invention to differentiation conditions, i.e., removal of mitogenic factors for two hours followed by exposure to TH-inducing media comprising the mitogenic factors EGF, bFGF, and LIF plus glial cell conditioned media resulted in TH-expressing neuronal cells (FIG. 5).

The glial conditioned media for use with the present invention may be prepared by conditioning media with glial cells and/or at least one glial derived soluble factor.

Where the glial conditioned media is prepared using glial cells, the glial cells may be derived from any population of glial cells, such as for example astrocytes or oligodendrocytes. As is known to those of skill in the art astrocytes are classified into two types of cells: type 1 astrocytes (antigenically Ran2$^+$, GFAP$^+$, FGFR3$^+$, A2B5$^-$) and type 2 astrocytes (antigenically A2B5$^-$, GFAP$^+$, FGFR3$^-$, Ran 2$^-$). While either type of astrocyte may be used to prepare the glial conditioned media of the present invention, type 1 astrocytes are preferred. In one embodiment, the glial conditioned media is prepared using the rat B49 glial cell line (not available commercially). Other cells lines that may be used within the context of the present invention include without limitation: glioma cell lines, the R33 and JS1 glial cells lines. See, e.g., Engele et al. J. NEUROSCI. RES. 30(2):359-371 (1991). Commercially available glial cell lines that may be used with the present invention may be obtained through the American Type Culture Collection (ATCC, Manassas, Va.).

Where the glial conditioned media is prepared using at least one glial derived soluble factor, the at least one glial derived soluble factor may be a glial derived peptide. In one embodiment, the glial derived peptide is selected from transforming growth factor beta (TGF-β) related factors and Wnt proteins. TGF-β related factors that may be used with the present invention include without limitation: glial derived neutrophic factor (GDNF), inhibins, activin, anti-muillerian hormone, bone morphogenetic protein (BMP), decapentaplegic, and Vg-1. Wnt proteins that may be used with the present invention include without limitation: Wnt-1, Wnt-2, Wnt-3, Wnt-4, Wnt-5, Wnt-6 and Wnt-8. As noted above, the glial conditioned media of the present invention may also be prepared with glial cells and at least one glial derived soluble factor. In one embodiment, the conditioned media may be prepared with astrocytes as the glial cells and one or more glial derived soluble factors selected from the group consisting of glial derived neurotrophic factor (GDNF), activin, BMP-2, and Wnt-1, Wnt-3, and Wnt-5.

In a further embodiment of the invention, the glial conditioned media comprises serum. It is understood by those of ordinary skill in the art that the addition of serum to culture media is helpful for cell growth.

The NSCs of the present invention have utility in a number of therapeutic applications.

In one aspect of the invention, the NSCs of the present invention may be used for repopulating stroke damaged tissue with neural cells comprising grafting the NSCs obtained according to the method of the present invention into lesioned brain of a subject that has suffered a stroke. In one embodiment of the invention, the NSCs may be grafted into the lesioned striatum of a stroke damaged brain; however, it is to be understood that the NSCs may be grafted into any area of a stroke damaged brain. As shown in Example 4, NSCs introduced into a stroke-damaged environment responded with pronounced migration and dispersion.

In another aspect of the invention, the TH-expressing neurons derived from the NSCs of the present invention may be used as a source of dopamine neurons for subjects suffering from dopaminergic dysfunction. As used herein, the term "dopaminergic dysfunction" is meant to include the loss of dopamine neurons or the loss of function of dopamine neurons. An example of a condition characterized by dopaminergic dysfunction is Parkinson's disease. In one embodiment of the invention, the TH-expressing neurons may be administered into the nervous system of a subject suffering from dopaminergic dysfunction. For example, where the subject is suffering from Parkinson's disease, the TH-expressing cells may be administered to the subject's basal ganglia.

In a further aspect of the invention, there is provided a method of screening a drug for therapeutic effects on dopaminergic cells comprising treating the TH-expressing neurons of the present invention with the drug and measuring the TH-expressing neurons for responses selected from the group consisting of dopaminergic response, cell survival, phenotypic changes, and genotypic changes.

In one embodiment of the invention, dopaminergic response is an ability of the TH-expressing neurons to produce or metabolize dopamine.

All patents and publications mentioned herein are incorporated by reference in their entireties.

It is to be understood that while the invention has been described in conjunction with preferred embodiments of the invention, the foregoing description of the invention is intended to illustrate and not limit the scope of the invention. In a similar vein, the following examples, which are intended as non-limiting examples of the invention, are put forth so as to provide those of ordinary skill in the art with a complete disclosure and description of how to make and use the claimed invention. Other aspects, advantages and modifications of the invention will be apparent to those skilled in the art to which the invention pertains upon a reading of the description or upon practice of the examples.

EXPERIMENTAL

In the examples that follow, efforts have been made to ensure accuracy with respect to numbers (e.g., amounts, temperature, etc.), but experimental error and deviations should be taken into account when conducting the described experiments. Unless indicated otherwise, parts are parts by weight, temperature is degrees centigrade and pressure is at or near atmospheric.

Unless otherwise indicated, all formulations described herein were performed with commercially available products. The following protocols were used in the Examples.

NSC culture media: The NSC culture media used in the Examples was prepared as serum free defined media composed of DMEM/F12 (1:1) including glucose (0.6%; Sigma-Aldrich Corp., St. Louis, Mo.), glutamine (2 mM; GIBCO®, Invitrogen, Carlsbad, Calif.), sodium bicarbonate (3 mM; Sigma-Aldrich Corp., St. Louis, Mo.), and HEPES buffer (5 mM; Sigma-Aldrich Corp., St. Louis, Mo.) plus the following hormone/salt mixture (all ingredients from Sigma-Aldrich Corp., St. Louis, Mo.): insulin (25 µg/mL), transferrin (100 µg/mL), progesterone (20 µM), putrescine (60 µM), and selenium chloride (30 nM), the latter in place of serum.

NSC defined media: The NSC defined media used in the Examples was the NSC culture media described above with the following mitogenic factors: 20 ng/mL EGF (Collaborative Research), 10 ng/mL bFGF (R&D Systems, Inc., Minneapolis, Minn.), and 10 ng/mL of LIF (R&D Systems, Inc., Minneapolis, Minn.).

Cell Culture Conditions: Incubation at 37° C. in a 95% air/5% $CO_2$ humidified atmosphere.

Glial cell conditioned media: Glial cell conditioned media was prepared from the B49 rat glial cell line (obtained as a gift). See, Daadi & Weiss, J. NEUROSCI. 19:4484-4497 (1999). B49 cells were cultured in DMEM/10% FBS until confluency. Confluent glial cell cultures were rinsed once with PBS and twice with serum free DMEM/F12 (1:1) with growth factors and hormone mix and replaced in the incubator with 20 mL of the same media. The conditioned media was collected after 24, 48, or 72 hours and centrifuged at 1000 g and 2000 g to remove cellular debris. The conditioned media was carefully removed, filtered, aliquoted, and stored at 80° C.

Immunocytochemistry: Mouse monoclonal antibodies and polyclonal antisera raised in different species and directed against neurotransmitter phenotypes and neuronal antigens were used as primary antibodies for indirect immunofluorescense. The following antibodies were used: polyclonal anti-tyrosine hydroxylase (1:1000; Chemicon or Pel-Freez); dopamine-β-hydroxylase (1:200; Chemicon or Pel-Freez); anti-b-tubulin class III (Tuj1 polyclonal 1:100; Aves); polyclonal antibodies against GFAP (1:1000; Advanced ImmunoChemical Co.); monoclonal anti-galactocerebrocide (GC 1:100; Chemicon); anti-CNPase (1:200; Aves); secondary antibodies raised in goat against mouse and rabbit immunoglobulins, conjugated to the fluorophore rhodamine isothiocyanate (RITC 1:200; Jackson Immunochemicals, West Grove, Pa.) or fluorescein isothiocyanate (FITC 1:100; Jackson Immunochemicals, West Grove, Pa.). Indirect immunocytochemistry was carried out in cells that had been cultured for 24 hours or longer on glass coverslips, which were fixed with 4% paraformaldehyde for 20 minutes followed by three washes in PBS, 10 minutes each. Following the PBS rinse, coverslips were processed for dual labeling and incubated with the primary antibodies generated from different species that were added together in PBS/10% normal goat serum/ 0.3Triton X-100 for 2 hours at 37° C. Following three rinses in PBS, secondary antibodies were applied in PBS for 30 minutes at room temperature (RT). Coverslips were then washed three times (10 minutes each) in PBS, rinsed with water, placed on glass slides, and cover slipped using Fluor- Save™ (Calbiochem) as the mounting medium. Fluorescence was detected and photographed with a Zeiss photomicroscope.

Morphometric analysis: The number of TH-immunoreactive (TH-IR) neurons was determined by counting the number per coverslip at 200× in 15 randomly chosen microscopic observation fields per coverslip. Within the same randomly chosen fields, the total numbers of β-tubulin-IR neurons and of live cell nuclei stained with DAPI (4',6-diamidine-2'-phenylindole dihydrochloride) were determined by examining the entire surface area of each coverslip at 400× magnification or counting the number of cells in 15 randomly chosen microscopic observation fields per coverslip. The total counts were then expressed as percent of the total DAPI stained nuclei or of the total number of cells expressing the neuronal marker class III β-tubulin. The data for the morphometric analyses are represented by mean±SEM of experiments performed three or four times on independent culture preparations, each performed in duplicate. Statistical analysis of the data was carried out using a one way ANOVA™ (Shepherd Medical Solutions, Canton, N.C.) and significance of intergroup differences was determined by applying Student's t-test. Differences were considered significant at $p<0.05$.

Total RNA Extraction: After removal of the culture media, plated cells were lysed in situ using 1 mL of TRIZOL® (Invitrogen, Carlsbad, Calif.) per well. Lysates from like samples were pooled and placed on ice for 15 minutes. Two-tenths volume of chloroform was added, shaken vigorously, and allowed to stand at RT for 5 minutes. The phases were separated in a clinical centrifuge spinning at 2500 rpm for 20 minutes. The aqueous phase was transferred into a fresh tube, an equal volume of isopropanol was added, the contents were mixed by inversion, and the RNA was allowed to precipitate overnight at −20° C. The following day, the tubes were centrifuged at 3500 rpm for 20 minutes, the supernatant was decanted off, and the pellet dissolved in 4M guanidinium isothiocyanate solution (GIBCO®, Invitrogen, Carlsbad, Calif.). The RNA was precipitated using two volumes of absolute ethanol and incubation at 3500 rpm for 20 minutes. The pellets were washed in 70% ethanol and the tubes were spun again. The air-dried pellets were dissolved in water and the concentration of each sample was determined spectrophotometrically.

RT-PCR: One microgram aliquots of total RNA from the cells were reverse transcribed in the presence of 50 mM Tris-HCl, pH 8.3; 75 mM KCl; 3 mM $MgCl_2$; 10 mM DTT; 0.5 mM dNTPs; and 0.5 µg oligo (dT) 12-18 (PHARMACIA®, Pfizer Health AG, Stockholm, SE) with 200 units of Supercript RNase H-Reverse Transcriptase (GIBCO®, Invitrogen, Carlsbad, Calif.). The following primers were used:

| | |
|---|---|
| TH-sense: | 5'-AGT-GCA-CCC-AGT-ATA-TCC-GC-3' |
| TH-anti-sense: | 5'-GTC-TGG-TCT-TGG-TAG-GGC-TG-3' |
| Nurr1-sense: | 5'-GTG-GTC-TTG-CAC-AGG-TTG-CAA-TGC-G-3' |
| Nurr1-anti-sense: | 5'-GCA-AGT-CAC-ATG-GGC-AGA-GAT-AGC-C-3' |
| Ptx3-sense: | 5'-CCA-ATG-CGT-TCC-AAG-AAG-AT-3' |
| Ptx3-anti-sense: | 5'-AAT-CTG-CAG-GAT-TCC-TCC-CT-3' |
| GAD-sense: | 5'-GCG-CCA-TAT-CCA-ACA-GTG-ACA-G-3' |
| GAD-anti-sense: | 5'-GCC-AGC-AGT-TGC-ATT-GAC-ATA-A-3' |
| 18S-sense: | 5'-GTG-GAG-CGA-TTT-GTC-TGG-TT-3' |
| 18S-anti-sense: | 5'-CGC-TGA-GCC-AGT-CAG-TGT-AG-3' |

Aliquots of cDNA equivalent to 40 ng of total RNA were amplified in 25 µL reactions containing 10 mM Tris-HCl, pH 8.3; 50 mM KCl; 1.5 mM $MgCl_2$; 50 pmoles of each primer; 400 µM dNTPs; and 0.5 unit of AMPLITAQ® DNA polymerase (Roche Molecular Systems, Alameda, Calif.).

PCR was carried out using the following thermal profile: 4 min at 94° C.; 1 min at 94° C.; 1 min at 60° C.; 2 min at 72° C. for 30-38 cycles; 7 min at 72° C.; and finally a soak a at 4° C. overnight.

The following day, 15 µL aliquots of the amplified products were run on a 2% agarose tris-acetate gel containing 0.5 µg ethidium bromide per mL. The products were visualized through a UV transilluminator, captured in a digital format using Quality One Gel Analysis software (Bio-Rad, Hercules, Calif.).

In vitro and in vitro experiments: NSCs from passage 5 to 21 were used in all in vitro and in vivo (e.g., transplantations) experiments.

Example 1

Devivation of NSCS From hESCS

Figure 1A:
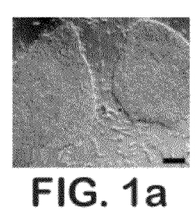
Figure 1B:
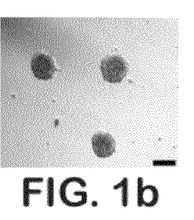
FIG. 1b shows primary neurospheres.

A stable homogeneous population of expandable multipotent NSCs was derived from the NIH-registered WA09 hESC line ("the H9 cell line"). The H9 cell line was expanded according to the supplier's protocol (FIG. 1a). After cell dissociation with collagenase, a portion of the H9 cell line was cultured in serum free media containing 20 ng/mL EGF, 10 ng/mL bFGF, and 10 ng/mL LIF. The defined media consisted of DMEM with F12 supplement (1/1) and the defined hormone mixture described above. After 3 days in vitro, the cells appeared aggregated in clusters or spheres in suspension with selective survival and growth (FIG. 1b). The dead cells were eliminated from the culture by selective centrifugation and the healthy spheres (primary spheres) were replated in fresh media with 20 ng/mL EGF, 10 ng/mL bFGF, and 10 ng/mL LIF.

Figure 1C:
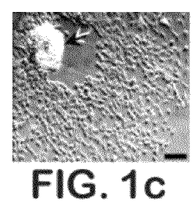
FIG. 1c shows attached primary neurospheres.
Figure 1D:
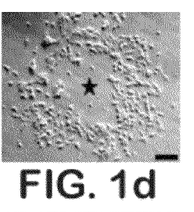
FIG. 1d shows the hollow core where the plated primary neurospheres detached to form secondary neurospheres.
Figure 1E:
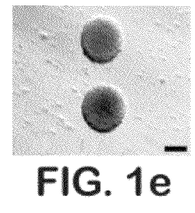
FIG. 1e shows the secondary neurospheres.

During the following week, the spheres of clustered cells attached to the flask and a fibroblastic-like cell population began to migrate out from them the attached clusters (FIG. 1c). Secondary spheres were generated from these cultures and lifted off by the end of the week leaving a hollow in the middle of the attached cells (FIG. 1d). The floating secondary spheres were collected and replated in fresh media with the same mitogenic growth factors for two weeks at which time they were collected and dissociated into smaller spheres/single cells. Following these steps, the isolated clusters of cells grew in a consistent and stable manner. The cultures were passaged by collagenase cell dissociation every 7 days in vitro for an additional four passages.

Figure 1F:
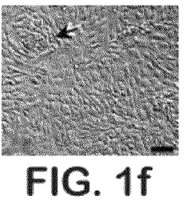
FIG. 1f shows the proliferation of the attached secondary neurospheres.

At the fifth passage, there was a change in the adherent properties of the cells, which began to grow as a monolayer with noticeable multiple foci of cells throughout the culture (FIG. 1f). Each focus originated from a central core suggesting their origin from a single NSC that would otherwise have given rise to a floating neurosphere. The monolayer culture of NSCs demonstrated clear contact inhibition of growth properties. As the cells were now adherent, single cell dissociation of the cells was carried out with trypsin-EDTA. At this stage, selective removal of mitogenic factors resulted in the inability of the NSCs to grow indicating normal non-transformed characteristics of the cells. The homogeneity of the NSCs cultured according to the method of the present invention is demonstrated in FIG. 1g; there, NSCs were stained with the nuclear marker DAP1 (top panel), the neural stem cell marker Nestin (bottom panel), and both markers (panel on the right). RT-PCR analysis confirmed that unlike hESCs, the undifferentiated NSCs did not express the pluripotency transcripts Oct-4 and Nanog (FIG. 1h).

Under the growth conditions specified herein, the NSCs showed stable growth and a consistent 2.7±0.2 fold increase every 5 to 7 days (FIG. 1l). The population doubling at each passage averaged 1.4±0.1 (FIG. 1m). The viability of NSCs at each passage was consistent at the approximate value of 98%. The projected cumulative cell numbers at each passage demonstrated that trillions of cells could be generated over a period of 5 months (FIG. 1l). The hESC-derived NSC lines described herein were expanded for over 20 passages with a stable differentiation profile.

Example 2

Testing for Self-Renewal of NSCS

To ascertain self-renewal ability under clonal conditions, the NSCs of Example 1 were single cell dissociated with collagenase and trypsin at passage 4 and greater and were plated at a clonal density of 10 cell/µL. To identify proliferating clones, cultures were fixed after 1, 2, and 7 day culture periods (FIGS. 1i-1k). After 48 hours, plated single cells underwent a first cell division and gave rise to the first progeny expressing nestin, a neuroepithelial stem cell marker. The single cell derived spheres continued to grow over the 7 days in vitro at which time all of the neurospheres generated expressed nestin indicating the neural purity of the isolated precursors. When induced to differentiate, the neurospheres consistently gave rise to neurons, astrocytes, and oligodendrocytes (FIG. 2). Under the culture conditions described herein, no rosette formation was observed during neural induction (c.f., U.S. Pat. No. 6,887,706 to Zhang et al.).

Example 3

Differentiation of the NSCS

Figure 2A:
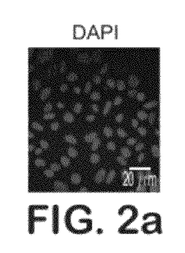
FIG. 2a shows the NSCs stained with the nuclear marker DAP1.
Figure 2B:
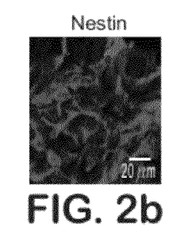
FIG. 2b shows the NSCs stained with the neural stem cell marker Nestin.
Figure 2C:
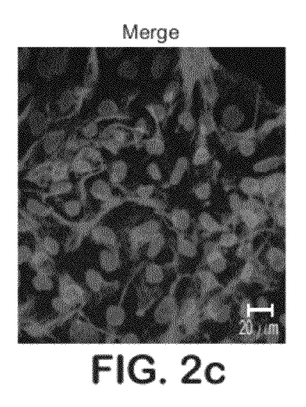
FIG. 2c shows the NSCs stained with both markers.

NSCs from the fifth and greater trypsin-EDTA passages of Example 1 were spun down and the supernatant was removed; the NSCs were resuspended in fresh media lacking the mitogenic factors and plated at a density of $5 \times 10^5$ cells/mL on poly-L-ornithine (PLO) coated (15 mg/mL; Sigma-Aldrich Corp., St. Louis, Mo.) glass coverslips in a 24 well Nunclon culture dish. Upon plating, the NSCs stopped proliferating and spontaneously differentiated into neurons, astrocytes, and oligodendrocytes consistent with normal neural precursor cell properties (FIGS. 2c-2e). After 2 days in vitro, 47.3±2.8% of the total population were nestin positive; 26.1±1.9% expressed the neuronal marker Tuj1; 30.3±2.1% expressed the astrocyte marker GFAP; and 8.7±0.8% differentiated into galactocerebrocide positive (GC+) oligodendrocytes. After 10 days in vitro, the proportion of nestin-positive cells decreased to 36.6±2.7; 62.5±2.8% expressed the neuronal marker Tuj1; 1.9±0.3% were GFAP+ astrocytes; and 7.1±0.4% were oligodendrocytes and expressed GC (FIG. 2b). Cell expression was determined using the immunocytochemistry method described above.

RT-PCR analysis confirmed that the transcript for the neural specific gene nestin was expressed by the NSCs. The neural cell adhesion molecule (N-CAM) transcript was induced in undifferentiated NSCs and expressed in differentiated NSCs (FIG. 2a). The NSCs did not express transcripts for brachyury and foxa2 marker genes for mesoderm and endoderm, respectively (data not shown). Upon removal of the mitogenic factors, the NSCs, expressed the lineage specific markers β-tubulin class III (Tub. III) and medium-size neurofilament (NF-M). Upon differentiation, the neurons expressed microtubule associated protein 2 (MAP-2), the astrocytes expressed GFAP; and the oligodendrocytes expressed myelin basic protein (MBP) (FIG. 2a).

Example 4

Repopulation of Stroke Damaged Tissue in NOD-SCID Mice

To determine the survival and engraftability of the NSCs of the present invention, NSCs from passage 10 were transplanted into the stratium of adult naive NOD-SCID immunocompromised mice and into immunosuppressed SD rats subjected to 1.5 hour of medial cerebral artery occlusion (MCAO). The transplanted cells were detected following one week and one month post-transplant survival time using the human nuclear specific marker hNuc.

Figure 3:
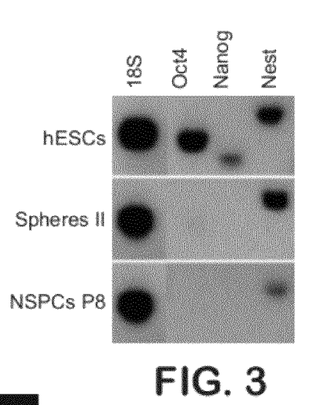
FIG. 3 shows gels from an RT-PCR analysis of the down regulation of the pluripotency transcripts Oct4 and Nanog in secondary neurospheres (Spheres II), and expanded NSCs at passage 8 (P8).

All the grafts survived and did not show any overgrowth sign or tumorigenesis (FIG. 3) and very rarely expressed the proliferative cell cycle marker Ki-67 (FIG. 3i). The grafts demonstrated a 12.3±1.1% survival and robust integration of the NSCs into host striatal parenchyma and extended long neurite outgrowth (FIG. 3e). The transplanted cells demonstrated a normal migration pattern in adult naive brain parenchyma characterized by controlled dispersion to the vicinity of the core graft (FIG. 3a). In migration-permissive structures, such as the corpus callosum, grafted NSCs showed elongated morphology of the nucleus typical of migrating cells (FIG. 3c). While in the parenchyma, the cell nuclei displayed round rested morphology after one month survival period (FIG. 3b) at which time, the grafted cells expressed nestin and adopted a mainly Tuj1+ neuronal phenotype with prominent long neurite outgrowths (FIG. 3e). Grafted NSCs also differentiated into CNPase-expressing oligodendrocytes (FIG. 3d) and rarely co-expressed the astroglial marker GFAP.

In the stroke lesioned rats, the grafted NSCs migrated and dispersed within the ischemia-damaged tissue, expressed nestin, and double cortin (DCX) in migrating neuronal precursors. The dispersion of the grafted cells was more pronounced in the animals with stroke-lesioned stratium than in the naïve animals.

Example 5

Expression of Nurr1 and Ptx3 in hESC Derived NSCS

NSCs cultured in the NSC culture media described above (control) and NSC culture media conditioned with glial cells and the mitogenic factors EGF, bFGF, and LIF (TH-inducing conditioned media) were harvested after 10 days in vitro and investigated for the presence of Nurr1 and Ptx3 transcripts. Semi-quantitative RT-PCR analysis revealed that the NSCs cultures in the TH-inducing conditioned media expressed significant numbers of Nurr1 and Ptx3 genes (FIG. 6) indicating that the hESC derived NSCs of the present invention have midbrain identity and thus, are a good source for dopaminergic neurons.

Example 6

Derivation of dopaminergic Neurons

Figure 4A:
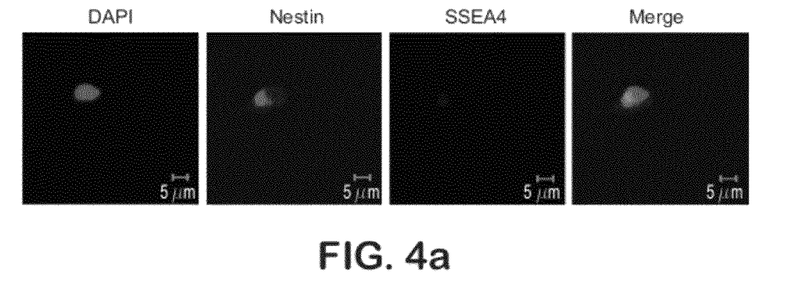
FIG. 4a shows the single cell stage.
Figure 4B:
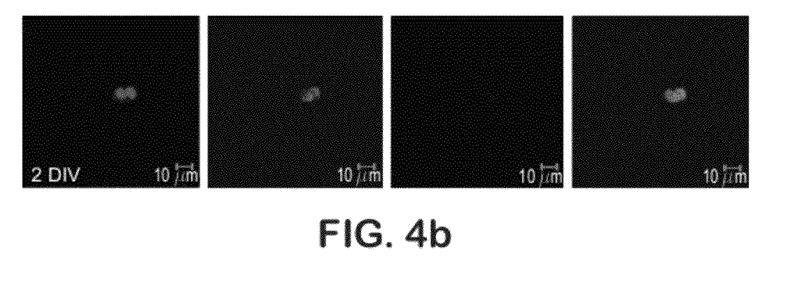
FIG. 4b shows the two-cell stage.
Figure 4C:
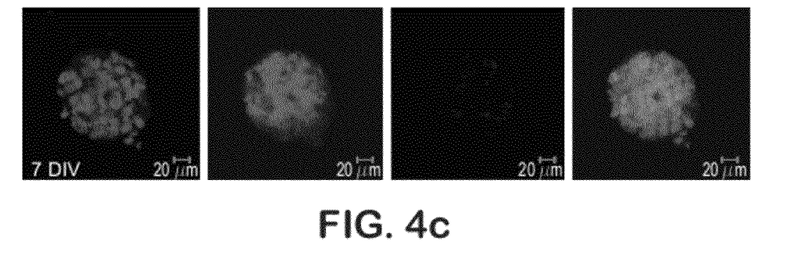
FIG. 4c shows the neurosphere stage.

To derive dopaminergic neurons from the NSCs of the present invention, the NSCs of Example 5 were single cell dissociated and induced to differentiate by culturing the NSCs in the NSC culture media described above (control) at $0.5 \times 10^6$ cell/mL, and plated at a density of $2.5 \times 10^5$ cell/cm² on PLO-coated (poly-L-ornithine) glass coverslips in 24-well culture dishes. The NSCs were allowed to adhere to the glass coverslips in order to initiate the differentiation process. After a 2-hour culture period, the NSC culture media was replaced by TH-inducing conditioned media containing 100% (v/v) glial cell conditioned media supplemented with 8 µg/mL heparin, 20 ng/mL EGF, 10 ng/mL bFGF and 10 ng/mL LIF. The cultures were incubated and investigated for TH induction within a period of 10 days in vitro. In each culture, the neuronal and dopaminergic lineage species were determined using immunocytochemistry for Tuj1 and TH, respectively. The cultures demonstrated a significant increase of the TH-IR (TH-immunoreactive) cells in cultures (FIGS. 4 and 5). After 10 days in culture, 16.8±2.4% of the total cells expressed TH, which represented approximately 27.6±4.0% of the total number of Tuj1-IR neurons.

Example 7

Figure 18:
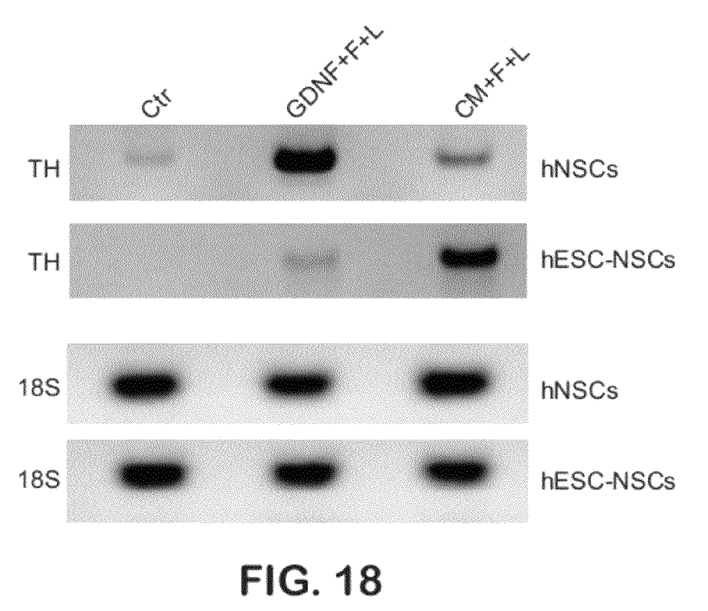
FIG. 18 is a photograph of a gel showing T11 expression of fetal brain NSCs (hNSCs) and human embryonic stem cells derived NSCs (hESC-NSCs) cultured in media enriched with glial derived neurotrophic factor (GDNF+F+L) and in glial conditioned media (CM+F+L).

Comparison of NSCS and hESC-NSCS Cultured in Non-Conditioned Media with Glial Derived Neutrophic Factor and in Glial Conditioned Media Tyrosine hydroxylase expression (TH) was measured in human neural stem cells derived from fetal brain (hNSCs) and from human embryonic stem cells (hESC-NSCs) cultured in NSC culture media defined with glial derived neutrophic factor (GDNF), bFGF, and LIF (GDNF+F+L) and in glial cell conditioned media with bFGF and LIF (CM+F+L). As shown in FIG. 18, the hNSCs cultured with the GDNF+F+L exhibited increased TH expression over the hESC-NSCs cultured with GDNF+F+L. By contrast, the hESC-NSCs cultured in CM+F+L exhibited increased TH expression over the hNSCs cultured in CM+F+L. The results of the experiment indicate that NSC culture media defined with GDNF, bFGF, and LIF is more potent in inducing TH expression in hNSCs than in hESC-derived NSCs while glial cell conditioned media with bFGF and LIF has stronger TH-inducing activity in hESC-NSCs than it does in hNSCs. Also shown in FIG. 18 is the control culture (18S), which shows strong TH-inducing activity in both hNSCs and hESC-NSCs under both culture conditions.

We claim:

1. A method of deriving a homogeneous population of human neural stem cells (NSCs) comprising the steps of:
    (a) culturing human embryonic stem cells (ESCs) as spheres in serum-free media comprising epidermal growth factor (EGF), basic fibroblast growth factor (bFGF), and leukemia inhibitory factor (LIF);
    (b) selecting and plating the spheres in a cell culture container in serum-free media comprising EGF, bFGF, and LIF until the spheres attach to the container and the cells form clusters; and
    (c) selecting and plating the clusters for a number of passages sufficient to change the adherent properties of the cells, wherein the cells grow as an adherent monolayer of nestin positive, homogenous, self-renewing cells.

2. A method of deriving a homogeneous population of human neural stem cells (NSCs) from embryonic stem cells (ESCs) comprising the steps of:
    (a) culturing an ESC line in serum-free media comprising epidermal growth factor (EGF), basic fibroblast growth factor (bFGF), and leukemia inhibitory factor (LIF) until spheres (primary spheres) form in the media;
    (b) selecting and plating the primary spheres in a cell culture container in serum-free media comprising EGF, bFGF, and LIF until the spheres attach to the container and the ESCs form clusters;
    (c) removing the clusters from the culture container and replanting the clusters as secondary spheres in a container with serum-free media comprising EGF, bFGF, and LIF, wherein the secondary spheres attach to the container; and
    (d) repeating step (c) for a number of passages sufficient to change the adherent properties of the cells, wherein the cells grow as an adherent monolayer of nestin positive, homogenous, self-renewing cells.

3. The method of claim 2, wherein step (c) is repeated with subsequent spheres until a population of cells of a desired concentration is obtained.

4. The method of claim 3, wherein the self-renewing cells express a neural progenitor stem cell marker.

5. The method of claim 4, wherein the neural progenitor stem cell marker is nestin.

6. The method of claim 4, wherein the NSCs are induced to differentiate by removal of EGF, bFGF, and LIF from the culture media and plating on a substrate.

7. The method of claim 6, wherein the substrate is coated with poly-L-ornithine (PLO).

8. The method of claim 6, wherein the differentiated NSCs to give rise to neurons, astrocytes, and oligodendrocytes.

9. The method of claim 8, wherein the neurons are identified by expression of a neuronal marker.

10. The method of claim 9, wherein the neuronal marker is Tuj1 (β-III-tubulin) or MAP-2 (microtubule associated protein 2).

11. The method of claim 8, wherein the astrocytes are identified by expression of an astrocyte marker.

12. The method of claim 11, wherein the astrocyte marker is GFAP (glial fibrillary acid protein).

13. The method of claim 8, wherein the oligodendrocytes are identified by expression of an oligodendrocyte marker.

14. The method of claim 13, wherein the oligodendrocyte marker is GC (galactocerebrocide) or MBP (myelin basic protein).

15. The method of claim 2, wherein the EGF, bFGF, and LIF are each present in the media in a concentration ranging from 1 µg/mL to 1 ng/mL.

16. The method of claim 1, wherein the number of passages sufficient to change the adherent properties of the cells is five or more.

17. The method of claim 2, wherein the number of passages sufficient to change the adherent properties of the cells is five or more.

* * * * *